United States Patent [19]

Scheu et al.

[11] Patent Number: 5,302,100

[45] Date of Patent: Apr. 12, 1994

[54] DRUM INSERT FOR A DEVICE FOR PRODUCING SHAPED PADS OF FIBROUS MATERIAL SURROUNDED ON ALL SIDES BY FOILS

[75] Inventors: Stephan Scheu; Armin Geisen, both of Neuwied, Fed. Rep. of Germany

[73] Assignee: Winkler & Dunnebier, Neuwied, Fed. Rep. of Germany

[21] Appl. No.: 889,383

[22] Filed: May 28, 1992

[30] Foreign Application Priority Data

May 29, 1991 [DE] Fed. Rep. of Germany ....... 4117662

[51] Int. Cl.$^5$ .............................................. B29C 33/30
[52] U.S. Cl. ................... 425/80.1; 425/183; 425/193; 425/220; 425/388
[58] Field of Search ............... 425/80.1, 81.1, 83.1, 425/183, 186, 192 R, 193, DIG. 60, DIG. 119, 373, 374, 363, 388, 220; 19/296

[56] References Cited

U.S. PATENT DOCUMENTS

| | | | |
|---|---|---|---|
| 3,846,871 | 11/1974 | Kolbach | 19/148 |
| 3,973,291 | 8/1976 | Kolbach | 19/148 |
| 4,592,708 | 6/1986 | Feist et al. | 425/80.1 |
| 4,674,966 | 6/1987 | Johnson et al. | 425/82.1 |
| 4,761,258 | 8/1988 | Enloe | 425/80.1 |
| 4,995,141 | 2/1991 | Gould | 425/80.1 |

FOREIGN PATENT DOCUMENTS 2238590 2/1973 Fed. Rep. of Germany .

Primary Examiner—Khanh Nguyen
Attorney, Agent, or Firm—Hoffman, Wasson & Gitler

[57] ABSTRACT

The present invention relates to the insert for the drum of a device for producing shaped pads from fibrous material. These inserts are attached to a disk of the drum and are designed in accordance with the shape and size of the pads to be produced. To simplify the retrofittability of the device or the drum for the production of pads of another size or shape and the number of drum inserts which must be kept in stock, it is provided that the drum insert consists of a base body, which, in turn, consists of a supporting sheet having several openings and several laminar sheets disposed in the direction of rotation of the drum and at right angles thereto. A forming insert is also provided at the outer side of the drum insert, which consists of a sieve and a sieve frame receiving it and that forming webs are provided in the drum insert which are located vertically above the laminar sheets extending transversely to the direction of rotation of the drum, whose shape is adapted to the shape of the sieve and thus to the shape of the pads to be produced in such fashion that the sieve retains its shape, even if it is loaded by the negative pressure.

6 Claims, 6 Drawing Sheets

DRUM INSERT FOR A DEVICE FOR PRODUCING SHAPED PADS OF FIBROUS MATERIAL SURROUNDED ON ALL SIDES BY FOILS

FIELD OF THE INVENTION

The invention relates to an insert for the drum of a device used to produce shaped pads of fibrous material surrounded on all sides by a foil.

BACKGROUND OF THE INVENTION

The aforementioned shaped pads may be sanitary towels for ladies, disposable diapers, incontinence products for adults or similar products. A device for their production is shown in U.S. Pat. No. 4,674,966, which uses a drum, which, in turn, is substantially designed as a rotatably mounted disk, to which drum inserts are successively fastened in the circumferential direction. These drum inserts form a cylindrical drum together with the disk. The drum inserts are components having the shape of segments of a circle, at whose outer circumference a forming recess is designed as a forming nest, whose bottom is of a sieve-shaped design, in order to be able to suck fibrous material into the forming nests by means of a negative pressure created in the interior of the drum. The shaped pads formed in this fashion are at first covered with a foil on one side. During further processing, the fiber pads become surrounded with a foil on all sides in the course of completion of the shaped pads. These drum inserts are milled out from a solid body, the sieve openings forming the bottom of the forming nests being designed as a plurality of bores. This construction of the drum inserts makes their production very expensive. Moreover, these inserts can only be used for the production of one size and one shape of shaped pads. A set of correspondingly, differently designed drum inserts must be manufactured and used for every other size and shape. The retrofitting of the drum in the case of the exchange of a set of specific inserts against another set of specific inserts is very time consuming and labor consuming, since this retrofitting must be carried out by hand and the drum inserts are very heavy.

SUMMARY OF THE INVENTION

Therefore, the present invention overcomes the deficiencies of the prior art by designing a drum insert in such fashion that the drum of a device for the production of shaped pads can be easily retrofitted to the production of shaped pads of another size and shape. Consequently, the number of sets of different drum inserts for retrofitting purposes of the device can be kept as small as possible and the drum inserts as such can be produced inexpensively.

As opposed to prior art inserts, the drum inserts according to the invention are not heavy inserts milled and bored from solid material, but are relatively light components, due to a rib-like construction of longitudinal webs, transverse webs, a bottom plate and an upper covering. Due to the arrangement of a changed number of transverse or longitudinal webs and by the provision of differently designed transverse webs or longitudinal webs, each individual drum insert can be easily retrofitted to the production of shaped pads differing in their shape and size.

Instead of such a retrofitting of individual inserts, drum inserts for the production of shaped pads differing in their shape and size can be combined using prefabricated, correspondingly, differently designed transverse and longitudinal webs, so that a relatively small storekeeping of sets of different drum inserts is necessary.

Moreover, the drum inserts according to the invention can be manufactured in inexpensive fashion, since the necessary transverse and longitudinal webs can already be produced in small series, for which purpose a numerically-controlled cutting machine can in particular be used, which would allow the automatic production of these webs, the bottom plate, the upper covering and the sieve insert of each drum insert. Even if the webs, bottom plate and covering plate, which are necessary for the construction of an individual drum insert, are firmly connected with each other, e.g. by means of spot welding, which is occasionally advantageous, in particular in view of a mutual allocation being as close as possible caused by the negative pressure applied to the interior of the drum, the drum inserts according to the present invention can be produced inexpensively since, even for the production of different drum inserts, a plurality of identical transverse and longitudinal webs can be used.

BRIEF DESCRIPTION OF THE DRAWING

The invention is described in detail in the following by means of a preferred embodiment exclusively by way of example and with reference to the drawings.

DETAILED DESCRIPTION OF THE INVENTION

For the production of shaped pads of fibrous material, such a material is sucked in by specially shaped openings in the area of the outer surface of a cylindrical drum. A negative pressure is produced in the interior of the cylindrical drum. The shape of the pads to be produced is determined by the shape of the arrangement of the sieve-like openings or the sieve-like openings must be designed and arranged in such fashion that they correspond to the shape of the pads to be produced.

Figure 1:
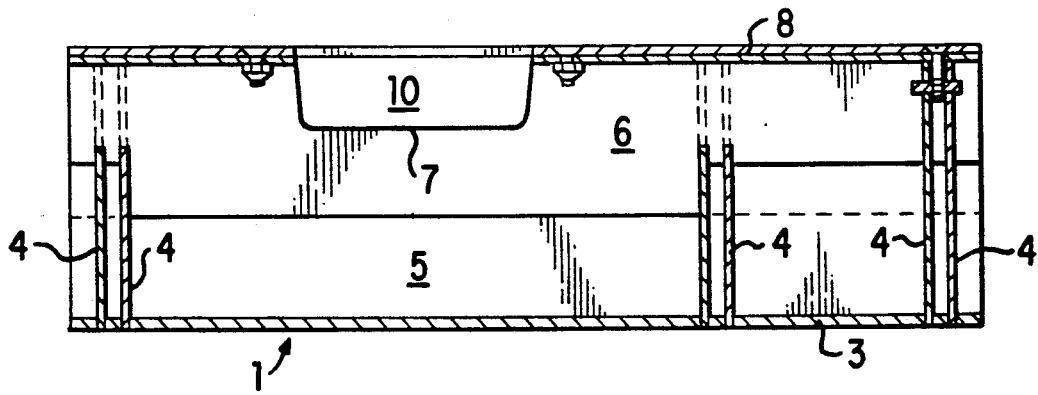
FIG. 1 shows a section along the line I—I of FIGS. 2 and 3 through a drum insert of a device for the production of shaped pads.
Figure 2:
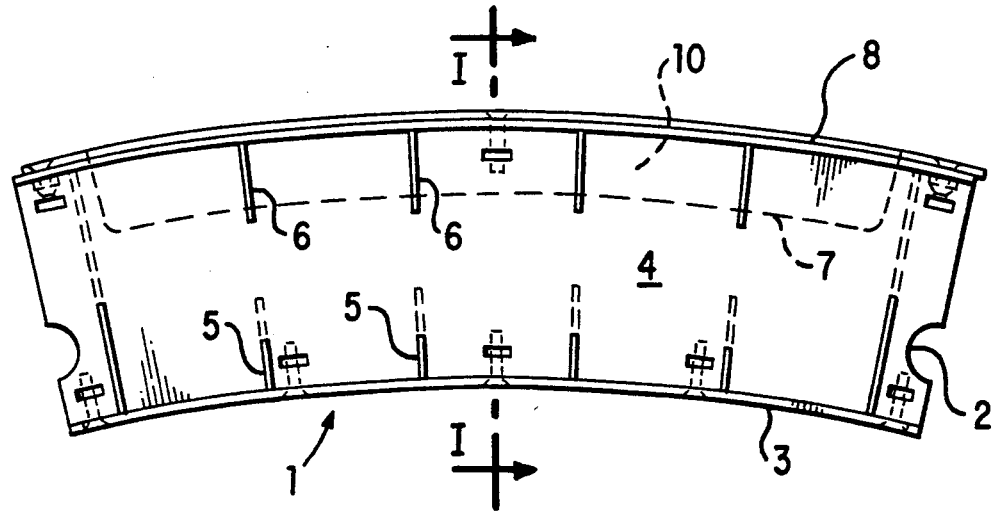
FIG. 2 shows a lateral view of the drum insert of FIG. 1 seen in the direction of the arrow A of FIG. 3.
Figure 3:
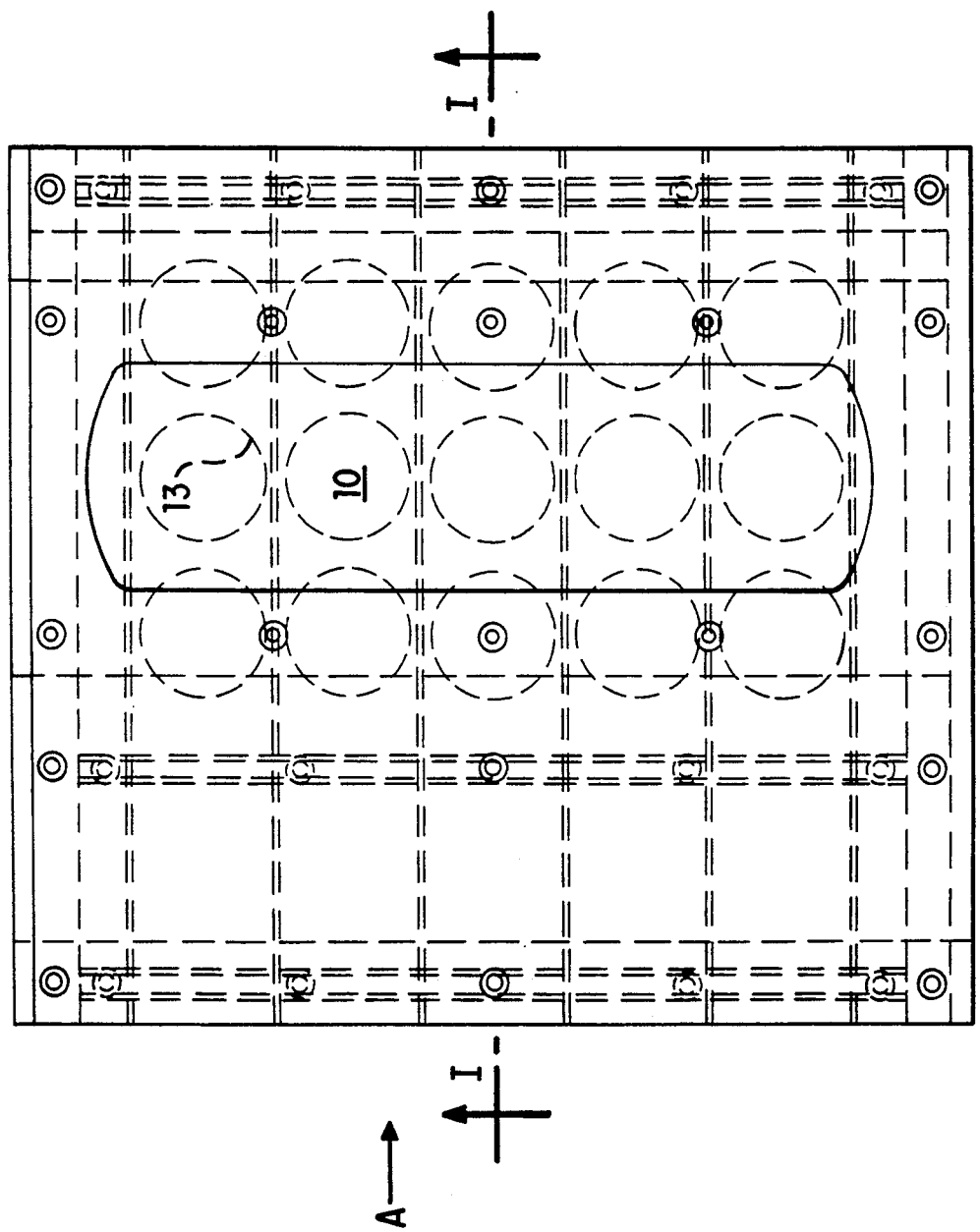
FIG. 3 shows the drum insert of FIGS. 1 and 2 in a view from outside the drum.

The cylindrical drum is built up of circular segment-shaped drum inserts 1 viewed in a circumferential direction. Such a drum insert 1 is represented in FIGS. 1-3 in different views or sections. FIG. 2 shows the circular segment shape of a drum insert 1 represented as a section and semi-circular cutouts 2, each at both ends for anchoring the drum inserts 1 at the guide rods of the drum body (not shown). The drum inserts 1 must be affixed on this disk by means of guide rods which are mounted on, for example, a circular disk of the drum. Due to a plurality of aligned drum inserts 1 at the guide rods of the drum body (not shown). The drum inserts 1 must be affixed on this disk by means of guide rods which are mounted on, for example, a circular disk of the drum. Due to a plurality of aligned drum inserts 1 in circumferential direction on the disk, the cylindrical drum can be constructed.

FIG. 1 shows a section through a drum insert 1, the sectional plate of FIG. 1 extending at right angles to the sectional plane of FIG. 2. The sectional plane of FIG. 1 is thus transverse to the direction or rotation of the cylindrical drum.

The drum insert 1 is constructed of a supporting sheet 3 and longitudinal webs 4 disposed in the direction of rotation of the cylindrical drum and transverse webs 5 disposed transversely to the direction of rotation. The longitudinal webs 4 and the transverse webs 5 extend radially outwardly from the supporting sheet 3. Forming webs 6 extending in the same direction are located vertically above the transverse webs 5, whose upper edge contour corresponds to the shape of the sieve 7 resting on the forming webs 6 or its frame 8, which can be seen in FIG. 2.

Figure 12:
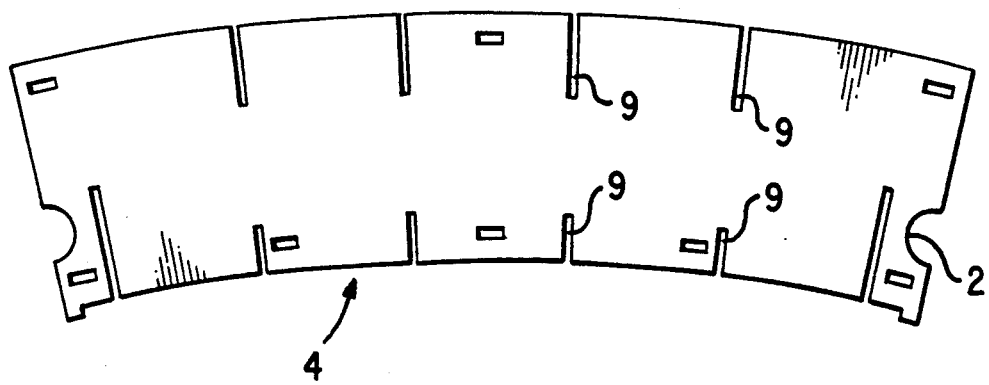
FIG. 12 shows a longitudinal web of the drum insert.

FIG. 12 shows narrow cutouts 9 in parallel to the longitudinal webs 4. These cutouts 9 serve for receiving the forming webs 6, inasmuch as the latter are located on the upper edge, or for receiving the transverse bars inasmuch as the latter are located on the lower edge. The sieve 7 and the sieve frame 8 form together a forming nest 10, which corresponds to the shape of the pads to be produced. Moreover, the forming webs serve for stabilizing the sieve shape against the negative pressure created within the cylindrical drum. The forming webs 6 and the forming nest 10 form the only product-specific or shape-specific elements of the drum insert 1.

These shape-specific elements can be simply removed or replaced by other elements. The sieve frame 8 at the outer edge of the drum insert 1 must only be removed for removal or dismounting. Since the sieve 7 is firmly connected with the sieve frame, e.g. screw-connected with it, the sieve 7 can be removed together with the sieve frame 8. Thereafter the forming webs 6 can be pulled out from the small cutouts 9 at the upper edge of the drum insert 1. For mounting, the aforementioned steps must be carried out in the reverse order. This shows clearly that not even the drum insert 1 as a whole must be dismounted from the cylindrical drum for a retrofitting of the drum in case of a change-over to the production of a product of another shape, but only the product-specific elements, namely the forming nest 10 which consists of sieve 7 and sieve frame 8, and the forming webs 6 must be exchanged.

If the individual elements of the drum insert 1 are connected with each other, e.g. by means of spot welding, each drum insert 1 provided at a drum must be removed and replaced by a drum insert with a differently designed forming nest for a retrofitting of the drum in the case of a change-over to produce a product of another shape.

Figure 9:
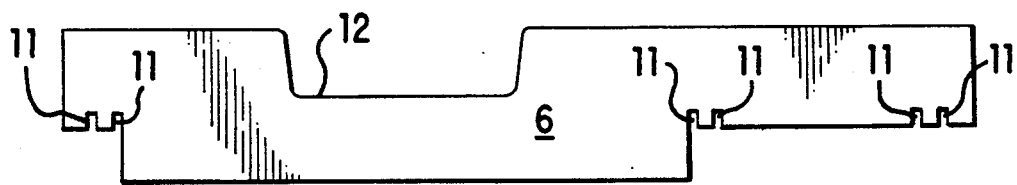
FIG. 9 shows a forming web of the drum insert.
Figure 6:
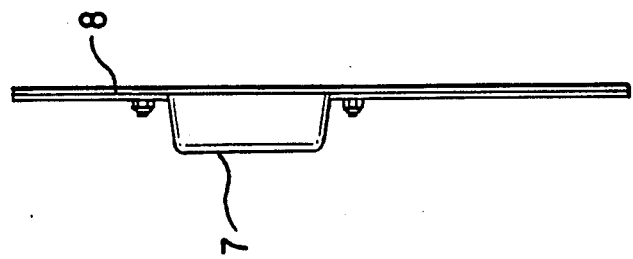
FIG. 6 shows the drum insert seen in the direction of the arrow C of FIG. 4.
Figure 5:
FIG. 5 shows the drum insert seen in the direction of the arrow B of FIG. 4.
Figure 4:
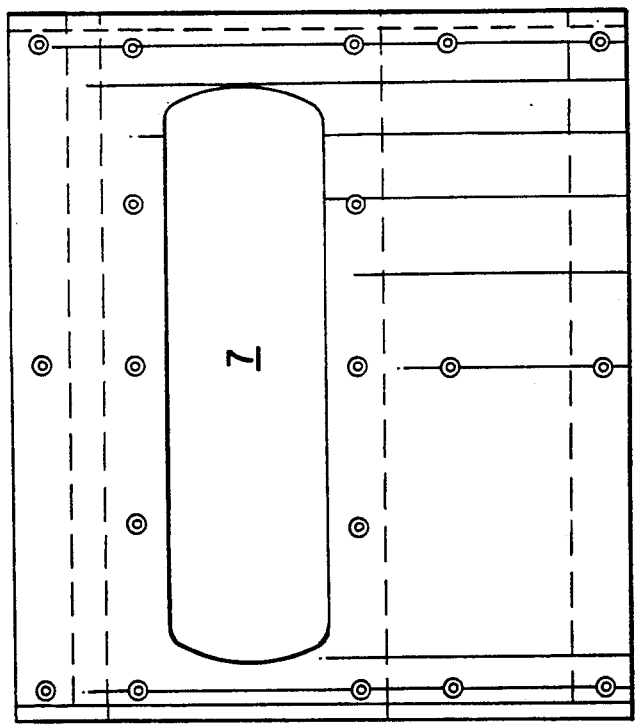
FIG. 4 shows a shaping insert affixed to the outside of the drum insert in a view from outside the drum.

FIG. 3 shows the drum insert 1 seen from above, i.e. from outside of the cylindrical drum. The opening of the sieve 7 determining the shape can be recognized within the sieve frame 8, which extends across the entire surface of the drum insert 1. FIGS. 4-6 show the forming insert forming the forming nest in three views, namely seen from outside of the drum and in two planes being at right angles to each other. FIG. 9 shows a forming web 6 with recesses 11 for the longitudinal webs 4 and a sieve recess 12. The shape of the sieve recess 12 is identical to the shape of the sieve, since the sieve shape is only supported by the forming web 6 against deformation at the negative pressure prevailing in the interior of the cylindrical drum.

Figure 13:
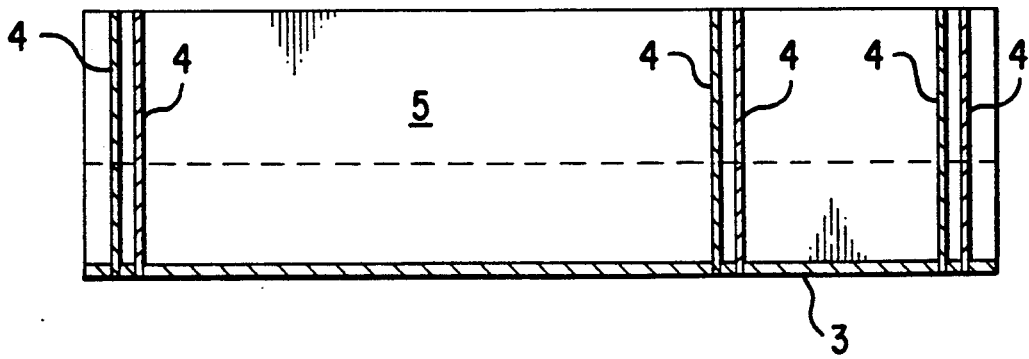
FIG. 13 shows a radial cross-section through the drum insert.
Figure 8:
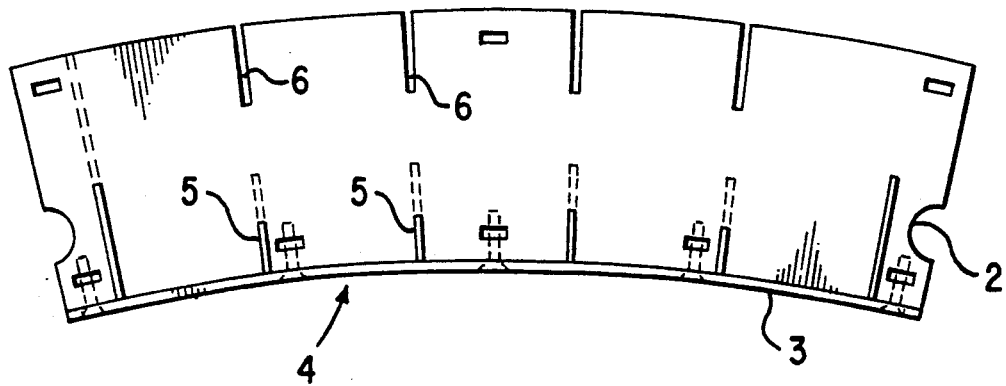
FIG. 8 shows a further lateral view of the drum insert.
Figure 7:
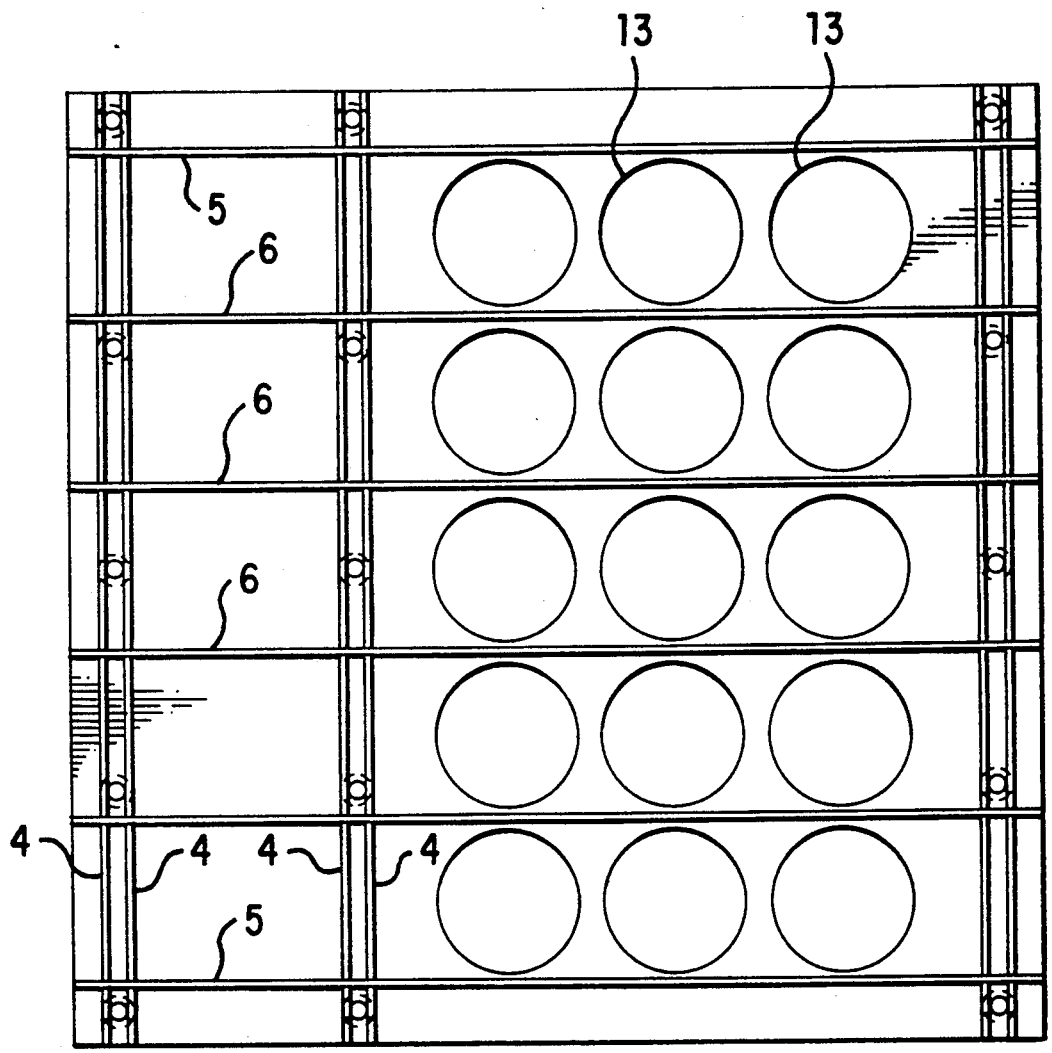
FIG. 7 shows a view of the interior of the drum insert.
Figure 10:
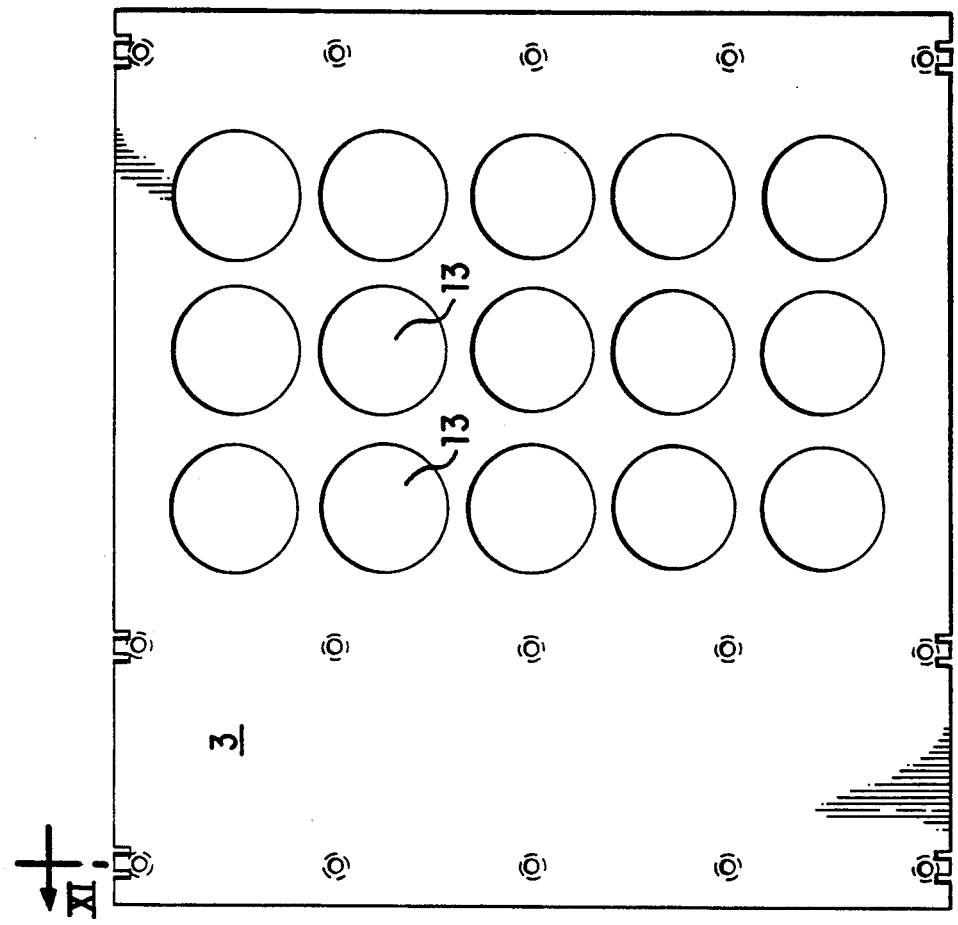
FIG. 10 shows a drum insert seen from within the drum.
Figure 11:
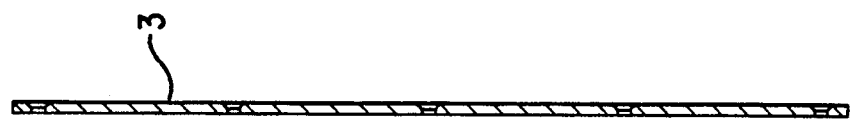
FIG. 11 shows a section along line XI—XI of FIG. 10 through the bottom plate of the drum insert.

FIG. 7 shows the interior of an opened drum insert 1. Openings 13 can be recognized in the supporting sheet 3 and the longitudinal webs 4 as well as the transverse webs 5 are shown. FIG. 8 shows the supporting sheet 3 of the drum insert 1 with its openings 13. FIG. 13 shows a lateral view of the drum insert 1 with simultaneous representation of the supporting sheet 3 and the longitudinal webs 4 disposed at right angles on it.

The special construction of the drum insert 1 from a series of parallel longitudinal webs 4 and a series of parallel transverse webs 5, ensures a high strength and stability of the drum insert 1 together with a simple producibility, since all longitudinal webs 4 and transverse webs 5 are identical to each other and can be practically produced in series production. If correspondingly firm sheet materials are used, there webs can be suitably produced by means of laser beam or water jet cutting. Both methods ensure a high precision of the shape to be observed with practically burr-free production of the webs.

Although the present invention has been described in detail, further improvements or modifications to the invention can be made without departing from the teachings of the present invention.

What is claimed is:

1. An insert for the drum of a device rotating in a first direction for producing shaped pads of fibrous material, the insert having a circular, segmented shape when viewed in an axial direction, the insert serving as the construction for the drum with a number of similar inserts to be affixed to a disk, to whose interior a negative pressure can be applied for the purpose of suction of the fibrous material therethrough to produce the shaped pads, comprising:

a planar supporting sheet serving as the base of the insert, said sheet provided with a plurality of holes therethrough;

a plurality of parallel longitudinal webs affixed to said planar supporting sheet, each of said longitudinal webs extending radially outwardly from said planar supporting sheet;

a plurality of parallel transverse webs affixed to said planar supporting sheet, each of said transverse webs extending radially outwardly from said planar supporting sheet, said planar supporting sheet, said plurality of parallel longitudinal webs and said plurality of parallel transverse webs forming a frame body for said insert;

a forming nest removably attached to said frame body, said forming nest including a sieve frame and a sieve provided within said sieve frame, said sieve corresponding to the shape of pads to be produced; and a plurality of parallel forming webs provided in said nest located vertically above said plurality of parallel transverse webs and supported by said frame body, each of said forming webs provided with an upper side, said plurality of parallel forming webs extending transversely to said first direction of rotation, and said plurality of parallel forming webs adapted to the shape of said sieve, and thus to the shape of the pad to be produced.

2. The insert in accordance with claim 1, wherein each of said parallel longitudinal webs is provided with a plurality of slots parallel to said first direction of rotation for the insertion of said plurality of parallel forming webs therethrough.

3. The insert in accordance with claim 1, wherein a recess is provided at said upper side of said plurality of parallel forming webs, whose shape corresponds to the shape of said sieve.

4. The insert in accordance with claims 2, wherein a recess is provided at said upper side of said plurality of parallel forming webs, whose shape corresponds to the shape of said sieve.

5. The insert in accordance with claim 1, wherein said plurality of parallel longitudinal webs and said plurality of parallel transverse webs are welded to said planar supporting sheet.

6. The insert in accordance with claim 5 wherein said plurality of parallel longitudinal webs and said plurality of parallel transverse webs are spot welded to said planar supporting sheets.

* * * * *